United States Patent [19]

Welsh et al.

[11] 4,181,613

[45] Jan. 1, 1980

[54] VENTING METHOD FOR A CHROMATOGRAPH OVEN

[75] Inventors: Paul B. Welsh, Wilmington; Stephen Van Lukas, Newark, both of Del.

[73] Assignee: Hewlett-Packard Company, Palo Alto, Calif.

[21] Appl. No.: 785,992

[22] Filed: Apr. 8, 1977

[51] Int. Cl.² .......................................... B01D 15/08
[52] U.S. Cl. .................................. 210/179; 55/197; 55/267; 55/386; 210/198 C; 432/199
[58] Field of Search ............... 55/197, 386, 208, 267, 55/269; 210/198 C; 432/42, 199, 200, 201; 219/391, 404

[56] References Cited

U.S. PATENT DOCUMENTS

| | | | |
|---|---|---|---|
| 2,963,898 | 12/1960 | Reynolds et al. | 55/386 |
| 3,053,077 | 9/1962 | Tracht | 55/269 X |
| 3,165,147 | 1/1965 | Roof et al. | 55/386 X |
| 3,305,000 | 2/1967 | Bullen et al. | 55/386 X |
| 3,422,603 | 1/1969 | Reynolds et al. | 55/386 |
| 3,563,006 | 2/1971 | Sutter | 55/267 |
| 4,038,055 | 7/1977 | Varano et al. | 55/197 |

Primary Examiner—John Adee
Attorney, Agent, or Firm—Donald N. Timbie

[57] ABSTRACT

An oven for a chromatograph is shown in which intake and exhaust ports are both located on the opposite side of the fan from the columns, and in such manner that ambient air entering through the intake port merges with hot air from the oven before reaching the columns.

4 Claims, 7 Drawing Figures

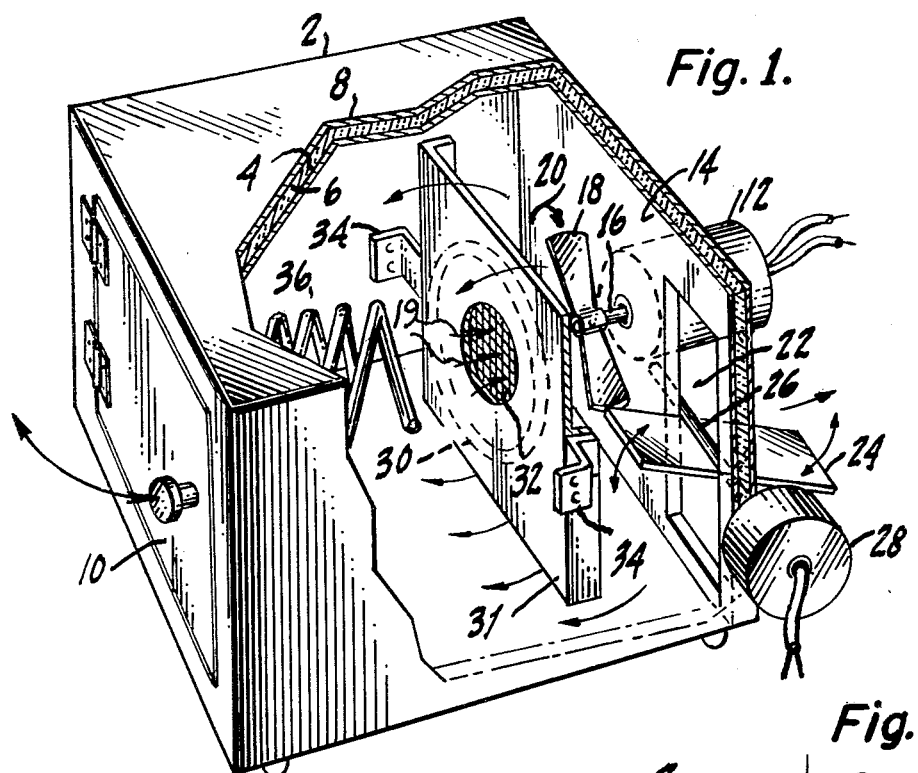

VENTING METHOD FOR A CHROMATOGRAPH OVEN

BACKGROUND OF THE INVENTION

This invention is concerned generally with chromatographs, and more particularly with the oven that contains the separating columns.

The basic components of a chromatograph are an injector for introducing a sample of matter to be examined into a stream of carrier medium, a column generally in the form of a helix of tubing containing chemicals that cause some of the constituents of the sample to elute at different times, an oven in which the column is mounted, a detector for producing a signal indicative of the concentration of the constituents being eluted, and an integrator for integrating the signal so as to provide information as to the quantity of each constituent.

A typical chromatograph oven comprises a thermally insulated housing having a door to permit the columns to be changed, a controlled heating element, and a motor driven fan. The fan continuously mixes the air within the housing so as to minimize temperature gradients therein that could adversely affect the performance of the chemical process occurring within the column.

In analyzing most samples, the heating element is controlled so as to increase the temperature of the oven from a minimum initial value to a maximum final value. Before introduction of the next sample into the column, the temperature of the oven is returned to its initial value. Whereas rapid cooling can be effected by simply opening the door, this heats up the front surfaces of the oven to an objectionable degree. It has therefore been arranged for the fan to draw cool ambient air into the oven through an intake port and to expel hot air from the oven through an exhaust port in such manner as to avoid heating the outer surfaces with which the operator is likely to come in contact. In prior ovens at least one of these ports has been located at a point remote from the fan so that the differential pressure between them is significantly less than is available near the fan. The resulting inefficiency has led to the use of large ports that require considerable force for adequate sealing around their long periphery.

In examining certain samples, however, it is desirable to maintain the oven at a selected temperature that lies in a range between that of the ambient air and the lowest temperature at which the oven can be stabilized when completely closed. Because of heat from the fan, heated injection ports and detector, the lowest stabilized temperature is about 25° C. above that of the surrounding ambient air. When operating at a lower temperature the fan draws cool ambient air in the intake port and expels it from the exhaust port in a controlled manner. In prior designs, the intake port has been so located that cool ambient air flows directly into the section of the oven occupied by the columns. A column is generally in the form of a helix of sufficient diameter to permit it to be oriented so that the entering cool ambient air flows through the center of the helix without creating temperature gradients in the column itself. It is often desirable, however, to use columns of such size and configuration that they cannot be mounted in the column section of the oen without being subjected to temperature gradients caused by the cool ambient air flowing over them.

BRIEF DISCUSSION OF THE INVENTION

In accordance with this invention, rapid cooling, steady operation close to the ambient temperature and exhausting of the hot oven air so that it does not interfere with the operator are all accomplished in such manner that the columns can be placed anywhere in the oven without subjecting them to undesirable temperature gradients. Rapid cooling can be achieved with intake and exhaust ports of small area by placing them near the points of lowest and highest oven pressures. Small ports can be sealed with little operating power. More important, however, is the fact that temperature gradients within the oven cavity are reduced to a minimum during operation at near ambient temperatures by merging the cool ambient air with warm air from the oven before it enters the column section of the oven.

BRIEF DESCRIPTION OF THE DRAWINGS

FIG. 1 is a partially broken perspective view of one embodiment of the invention wherein the intake and exhaust ports are contained within a single opening in the rear wall of the oven, FIG. 2 is a top view of the oven shown in FIG. 1 with the top removed, FIG. 3 is a view of section 3—3 of FIG. 2, FIG. 4 is an enlargment of section 4—4 of FIG. 2.

Figure 5:
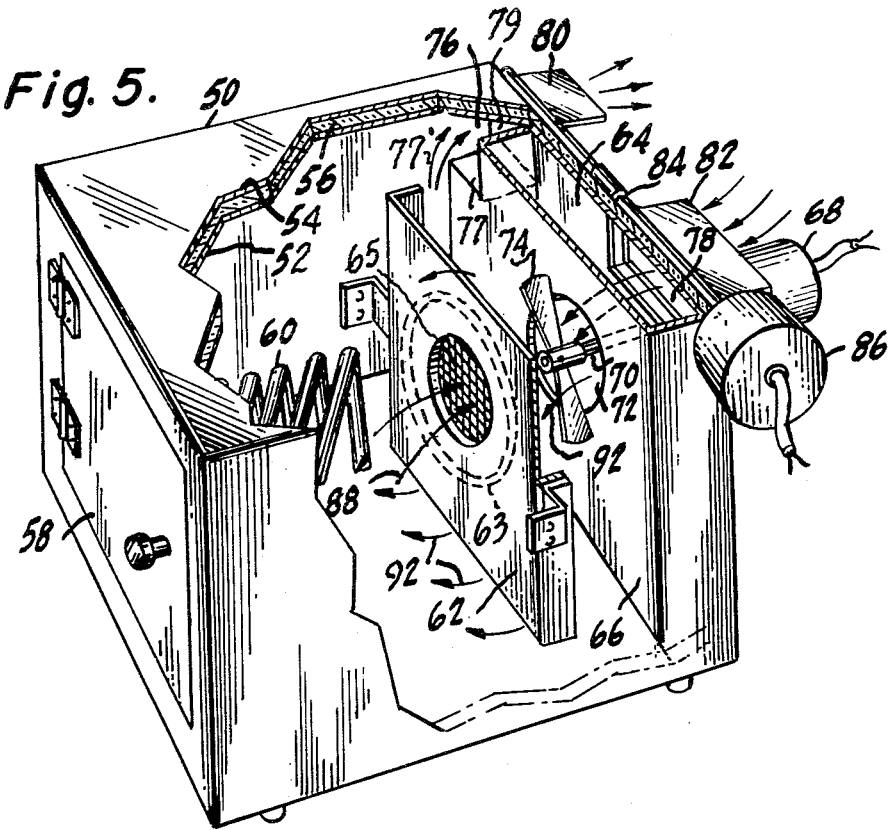
FIG. 5 is a perspective view that is partly broken away of another embodiment of the invention wherein the intake and exhaust ports are provided at separate openings in the rear wall of the oven.

Reference is made to FIG. 1 which shows an oven in the form of a rectangular box 2 having thermal insulation 4 between an inner metal shell 6 and an outer metal shell 8 and having a door 10 in the front side. It will be understood that the structure now to be described could be located at any side of the oven, but as shown it is located at the rear wall. A motor 12 is mounted at the approximate center of the rear wall 14 with its shaft 16 perpendicular thereto. A fan 18 is mounted on the shaft 16 and is rotated thereby in the direction of the arrow 20. The rear wall 14 of the oven defines a rectangular opening 22. A flap 24 is provided with its center attached to a horizontal shaft 26 of a motor 28. The shaft 26 exends horizontally across the middle of the opening 22. For reasons that will be explained, the upper half of the opening acts as an exhaust port and the lower half as an intake port. If the fan 18 rotated in the opposite direction, the reverse would be true. Although not shown, a duct is usually attached to the exhaust port so as to prevent hot exhaust air from being immediately drawn into the intake port. A heater wire 30, not shown, is located, as indicated by the dotted lines, on the rear side of a shroud 31. The shroud 31 has a central opening 32 therein and is mounted by tabs 34 in a plane parallel to the rear wall 14 and the door 10 at a point just forward of the fan 18. The shroud 31 is smaller than the cross section of the oven so that a space exists between its periphery and the inner shell 6 of the oven. Although a number of columns are generally mounted in the oven cavity only one column 36 is shown. As is customary, it is in the form of a helix and is mounted with its axis aligned with the shaft 16 of the motor 12. The oven cavity is comprised of two sections, one for the column 36 and the other for the fan 18, the dividing line between them being an imaginary plane touching the front edges of the blades of the fan 18 and perpendicular to a forward extension of the shaft 16. The purpose of the shroud 31 and the screen across its central opening 32 is to prevent an operator from touching either the heater 30 or the fan 18. As far as the invention is concerned, the heating wire 30 could be mounted near the inner shell 6 of the oven in the same plane as the shroud 31.

FIG. 2 is a top view of the oven illustrated in FIG. 1 with the top removed. From this it can be seen that the heating wire 30 is spaced from the rear of the shroud 31 and that the ends of the blades of the fan 18 just miss the flap 24. If the oven is used with a gas chromatograph, samples of the matter to be analyzed are supplied in gaseous form by a sample supply means 38 to an injector 40 wherein they are mixed with a carrier gas from a source 42 before being applied to one end of the column 36. Activity within the column 36 causes various constituents in the sample gas to elute from the other end at different times. The elutants are applied to a detector 44 that produces a signal related to their concentration. The signal from the detector is usually applied to an integrator, not shown, for determining the quantity of the matter eluted.

FIG. 3 is a view at section 3—3 of FIG. 2 for the purpose of illustrating the shroud 31, the heating wire 30, and the fact that there is a space between the periphery of the shroud 31 and the inner shell 6 of the oven. In this view the top is removed, but the portion of the shell 6 associated with the top would lie along the line 46.

FIG. 4 is a section 4—4 of FIG. 2 illustrating one construction of the flap 24. It is attached along its horizontal center to the shaft 26 of the motor 28. When in the position shown in solid lines, both top and bottom halves of the opening 22 are closed, but as the shaft 26 rotates to the position shown in dotted lines, the effective opening for the top and bottom halves of the opening 22 increases. For reasons to be explained, with the direction of fan rotation being as indicated by the arrow 20, the top surface of the flap 24 and the edge of the top half of the opening 22 define an exhaust port, and the bottom surface of the flap 24 and the edge of the bottom half of the opening 22 form an intake port.

OPERATION

When analyzing certain chemicals, a smaple is injected into the column 36, the oven door 10 is shut, the flap 24 is usually shut, and the current through the heater winding 30 is programmed by means not shown so as to increase the temperature of the oven from low initial value to a high final value. The fan 18 draws hot air to it from within a first zone in the oven cavity including the central portion of the column section of the oven cavity, as indicated by the arrows 19, and directs it along intermediate paths, such as indicated by the arrows 48, that extend along the blades of the fan 18 in a generally outward direction and pass by the heater 30. At the space between the shroud 31 and the inner shell 6 the hot air reenters the column section of the oven within a second zone next to the inner shell 6 of the oven cavity. After passing forwardly through the second zone, as indicated by arrows 49, the air reenters the first zone as indicated by the arrows 49'. Thus the flow of air in the oven cavity is in the form of a vortex.

Before the next sample is introduced into the column 36, the oven must be cooled down and stabilized at the initial temperature. To do this as rapidly as possible the flap 24 is fully opened to a position shown by the dotted lines in FIG. 4. A portion of the hot air flowing in some of the intermediate paths 48 is intercepted by the upper surface of the inner end of the flap 24 and directed out the top half of the opening 22. This creates a partial vacuum in the space below the flap 24 that draws in cool ambient air. The cool ambient air merges with the portion of the hot air flowing in the intermediate paths that was not intercepted by the flap 24 and enters the second zone near the outside of the oven. Because of the location of the flap 24 a large differential is developed between the high pressure in the top half of the opening 22 and the low pressure at the bottom half.

During rapid cooling as just described, no analysis is being performed so the fact that means including the flap 24 and opening 22 are provided for causing the cool ambient air to mix with warm air in the intermediate paths 48 before reaching the second zone in the column section of the oven cavity is of no consequence, but when making analyses at a near ambient temperature, the merging with warm air is of great importance as the cool air can be warmed before reaching the columns, regardless of their locations. This minimizes temperature gradients to which a column is subjected. During operation at near ambient temperatures, the position of the flap 24 is varied so as to set the ratio between hot exhaust air and entering cool ambient air as is required, and the heat supplied by the heater wire 30 may be programmed by means not shown so as to warm the mixture of cold and hot air as needed. The flap can be rotated to any desired position by the motor 28 without requiring much power.

SECOND EMBODIMENT

FIG. 5 shows a rectangular box-like oven 50 having an inner metal shell 52 separated from an outer metal shell 54 by a layer of insulation 56. A door 58 is mounted in the front side of the oven 50, and an helical column 60, a shroud 62, and a heater 63 are mounted in the same manner as shown in FIG. 1. The shroud 62 has a central opening 65 covered by a screen. Parallel to and spaced forwardly of the rear outside wall 64 of the oven housing is the rear wall 66 of the oven cavity. A motor 68 is mounted on the outside of the rear wall 64 of the housing with its shaft 70 perpendicular thereto and extending through the rear wall 64 and through an intake port 72 in the rear wall 66 of the oven cavity. A fan 74 is mounted on the shaft 70 foward of the wall 66 and behind the shroud 62. Similar to the embodiment shown in FIGS. 1-4, the oven cavity within the inner shell 52 is comprised of a fan section and a column section divided by an imaginary plane touching the forward edges of the fan 74 and perpendicular to an extension of the shaft 70. A duct 76 forms a passageway between an exhaust port 77 in the rear wall 66 of the oven cavity and an opening 79 in the rear wall 64 of the oven housing, and the space between the rear walls 66 and in a duct 64 forming a passageway between the intake port 72 and a second opening 78 in the rear wall 64. Flaps 80 and 82 are connected to a shaft 84 of a motor 86, and as can be seen more clearly in FIG. 7, the shaft is mounted along the top of the rear wall 64 so that it can rotate the flaps 80 and 82 so as to open or close the openings 79 and 78. The partition 66 could be the rear wall of the oven, but the positions of the intake port 72 and the exhaust port 77 are such that a more complicated mechanism to open and close them would be required.

OPERATION

Figure 6:
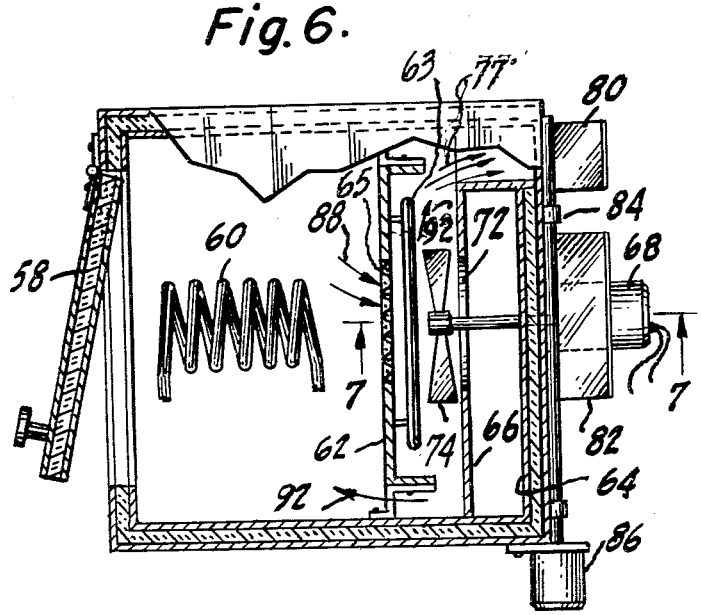
FIG. 6 is a top view of the oven shown in FIG. 5 with the top removed.
Figure 7:
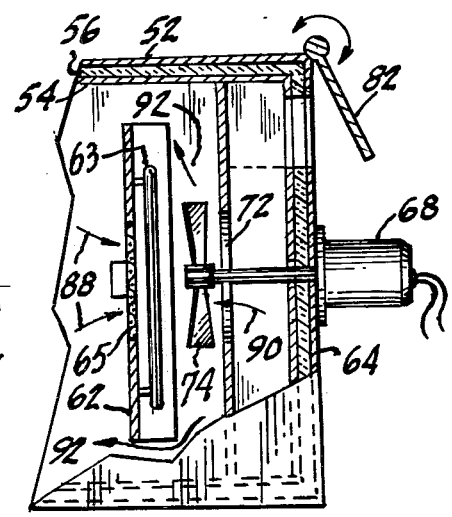
FIG. 7 is a view of section 7—7 of FIG. 6.

When the oven of FIGS. 5, 6, and 7 is being used for making analyses during temperature runs from a low initial value to a maximum value, the door 58 is closed and the flaps 80 and 82 are usually closed. Under this condition the flow of air in the first and second zones of the column section of the oven cavity and in the intermediate paths in the fan section of the oven cavity is in the form of a vortex as described in connection with FIGS. 1–3.

In order to cool the oven as rapidly as possible, the flaps 80 and 82 are rotated to a fully open position. The intake port 72 is located around the shaft 70 of the motor 68 where the pressure is lowest, and the exhaust port 77 is at a corner of the oven cavity, where the pressure is the highest. The other corners of the oven would have equally high pressure, but it has been found that communication with only one produces good results. Cool ambient air is drawn by the fan 74 through the opening 78 into the space between the rear wall 64 of the housing and the rear wall 66 of the oven cavity. The cool ambient air then passes through the intake port 72 in the rear wall 66 of the oven cavity and merges with hot air from the oven flowing in the intermediate paths, such as 92. The mixture of hot and cold air is directed by the fan 74 is a generally outward direction so as to pass by the heater 65 and around the shroud 62 before entering the second zone in the column section of the oven cavity. Some of the air drawn by the fan 74 from the central or first zone of the oven through the opening 65 is directed along an intermediate path 92 to the exhaust port 77, through the duct 76 and out to the outside atmosphere through the opening 79. As the temperature in the oven drops toward the desired initial temperature, the flaps 80 and 82 are gradually closed so as to prevent the oven from dropping below the initial temperature.

When operating at a near ambient temperature, the flaps 80 and 82 control the ratio of the hot oven air exhausted through the exhaust port 77 to the cool ambient air drawn in the intake port 72 so as to aid in establishing the temperature of the oven at any desired value. The fact that the cool ambient air merges with some of the hot oven air flowing along intermediate paths such as indicated by the arrows 92 before entering the column section of the oven cavity makes it possible to mount a column anywhere within that section without its being subjected to temperature gradients.

In the embodiment of the invention of FIGS. 1–4 or the embodiment of FIGS. 5–7 the intake and exhaust ports can be respectively located at low and high pressure points at any point back of the plane at the front edges of the fan so as to be remote from the columns which are mounted forward of this plane. The shape of the ovens shown is rectangular but the oven could have other shapes such as a cylinder wherein the circular faces form the front and rear of the oven. The heaters may be mounted in a number of places, but it is only important that air flow across them from the fan.

We claim:

1. A chromatograph oven comprising,
    a housing having rectangular front, rear and four side walls defining a cavity within them,
    an inner rear wall in said cavity spaced from said rear wall of said housing,
    a door mounted in said front wall of said housing,
    a fan mounted for rotation within said cavity about an axis extending through central sections of said front and rear walls of said housing,
    means defining an exhaust port in said inner rear wall of said cavity at a corner of said rear wall,
    a first duct extending through said housing from the means defining said exhaust port so as to communicate between said cavity and ambient air,
    means defining an intake port about the axis of said fan in said rear wall of said cavity,
    a second duct extending through said housing from said means defining said intake port so as to communicate between said cavity and ambient air,
    means including a first flap for opening and closing said first duct, and
    means including a second flap for opening and closing said second duct.

2. A chromatograph oven comprising
    an oven housing comprised of a plurality of adjoining exterior walls defining a given volume within them,
    an interior wall mounted in said volume and in spaced relationship with one of said exterior walls and in contact with the other exterior walls so as to define an oven cavity between one side of said interior wall and the inside of the other exterior walls, and so as to define a space between the other side of said interior wall and said one exterior wall,
    means defining a central opening in said interior wall,
    means mounting a fan for rotation in said oven cavity about an axis extending through said central opening,
    means defining an opening in said interior wall at a point having a different pressure than exists at said central opening when said fan is rotating,
    means defining a first opening in the portion of an exterior wall lying on the side of said interior wall opposite to said oven cavity,
    a duct connected between said opening in said interior wall and said first opening in said exterior wall so as to communicate between said oven cavity and ambient air outside said oven housing, and
    a second opening in the portion of an exterior wall lying on the side of said interior wall opposite to said cavity, said second opening communicating between the space between said interior wall and said one exterior wall and the ambient air outside said housing.

3. An oven as set forth in claim 2 wherein
    said first and second openings are aligned on the same exterior wall,
    a shaft is mounted for rotation on said exterior wall and extends past said first and second openings, and
    flaps are mounted on said shaft whereby rotation thereof causes said flaps to open or close said first and second openings.

4. A chromatograph oven comprising
    a plurality of walls defining a closed cavity,
    a door mounted in a first of said walls,
    a fan having blades of a given length extending radially from a first axis so that when rotated about the first axis it draws air to it along the axis and thrusts it in a generally outward radial direction along the blades,
    means mounting said fan for rotation about said first axis with said first axis perpendicular to a second of said walls, means defining an opening in said second wall, said opening being farther from said first axis than the radial length of said blades of said fan,
a flap,
means mounting said flap for rotation about a second axis extending across said opening, the length of said flap on one side of said second axis being sufficient to permit it to be rotated to position where it intercepts air thrust outwardly by the blades of said fan and guides it through the portion of said opening on one side of said second axis, thereby creating a lower pressure in the portion of said opening that is on the other side of said second axis.

* * * * *